United States Patent [19]

Brassell

[11] Patent Number: 4,957,518

[45] Date of Patent: Sep. 18, 1990

[54] ASSEMBLY USEFUL FOR RETAINING COMPONENTS SUCH AS A FILTER TO A CONTAINER AND A CORRESPONDING COMBINATION

[76] Inventor: Gilbert W. Brassell, 13237 W. Eighth Ave., Golden, Colo. 80401

[21] Appl. No.: 362,152

[22] Filed: Jun. 6, 1989

[51] Int. Cl.⁵ .......................................... B01D 53/04
[52] U.S. Cl. .................................. 55/316; 55/385.4; 55/502; 55/510; 55/518
[58] Field of Search ............... 55/385.4, 504, 503, 55/510, 511, 517, 518, DIG. 2, 159; 604/333

[56] References Cited

U.S. PATENT DOCUMENTS

| | | | |
|---|---|---|---|
| 2,555,086 | 5/1951 | Guinn | 604/333 |
| 2,918,064 | 12/1959 | Booth et al. | 604/333 X |
| 3,880,625 | 4/1975 | Shook | 55/502 X |
| 4,229,193 | 10/1980 | Miller | 55/DIG. 2 X |
| 4,391,873 | 7/1983 | Brassell | 423/447.2 X |
| 4,512,771 | 4/1985 | Norton | 55/385.4 X |
| 4,516,974 | 5/1985 | Davis | 604/333 |

*Primary Examiner*—Charles Hart
*Attorney, Agent, or Firm*—Millen, White & Zelano

[57] ABSTRACT

An assembly retains an element such as a filter in a vent opening of a waste disposal bag which can contain hazardous materials such as nuclear waste. The assembly includes a base plate and a cap plate. The base plate and cap plate cooperate to define a chamber for holding the filter element and to sandwich therebetween a portion of the bag adjacent the vent.

24 Claims, 2 Drawing Sheets

ASSEMBLY USEFUL FOR RETAINING COMPONENTS SUCH AS A FILTER TO A CONTAINER AND A CORRESPONDING COMBINATION

BACKGROUND OF THE INVENTION

The instant invention relates to an assembly useful for retaining components such as filters, deodorizers, desiccants, chemical reactants, absorbents, adsorbents, indicators, etc., to a wall, e.g., of a container such as a bag, and to the combination of the assembly with the component and, e.g., a container. More particularly, the instant invention relates to an assembly preferably for retaining a filter wherein the filter or other component is used in combination with a wall, e.g., of a container, such as, for example, a waste container (e.g., a plastic bag), wherein the waste therein contains contaminated gases, e.g., radioactive contaminated gases.

Disposing of hazardous waste has become a critical problem in modern societies. One proposal is to contain hazardous waste in plastic bags either temporarily or permanently for storage and disposal. If the waste contains and/or emits innately hazardous gases, then the safety of hazardous waste stored in plastic containers or the like is compromised.

Considering a first specific example, nuclear waste materials emitting relatively low-level but still dangerous amounts of radiation are retained in walled containers, especially flexible plastic bags. It is desirable to vent the bags in order to minimize the danger of gases building up in and perhaps bursting them. Since the bags are vented to the atmosphere, the gases may carry with them minute radioactive particles which pose a serious health hazard, and, e.g., can be inhaled. It is, therefore, very important to properly filter the gases venting from storage bags for nuclear waste.

Bags for storing other waste are also preferably vented. Exemplary of such bags are the bags used to store human waste after a colostomy operation.

In view of the aforedescribed problems in storing waste materials, there is a need for a safe, durable and convenient way to vent such containers while minimizing the risk of releasing contaminated particles or other contaminants into the atmosphere.

SUMMARY OF THE INVENTION

This invention minimizes the risk of venting containers such as plastic bags containing materials which may contain or release gases containing dangerous contaminants and also provides a convenient means to retain components such as filters and other devices to a wall.

The instant invention contemplates an assembly for retaining a component such as a filter on a wall, e.g., of a container, e.g., wherein the container contains materials, such as waste materials, which may contain or emit hazardous or otherwise undesirable gases. The assembly for retaining the component includes a base plate and a cap. The base plate has a chamber-defining flange projecting therefrom which defines a chamber in which a component such as a filter is contained. The cap interlocks with the chamber-defining flange to hold the filter or other component in the chamber defined thereby. The base plate and cap both have rim flanges which project beyond the chamber-defining flange, which rim flanges overlie one another. A pair of gaskets are preferably disposed between the rim flanges for sealing against the portions of the container adjacent the vent opening where such sealing is desired, e.g., in the case of hazardous gas filtering. It is also possible for only a single gasket to be used or even no gaskets where the wall itself provides an effective seal. Other sealing materials may also be used.

Both the base plate and cap can have openings therethrough, e.g., to allow gases within the container to flow into a filter-containing chamber, through the filter itself and out into the atmosphere so that the particles or other hazardous substances are trapped by the filter and remain contained therein. Similar designs will be useful for deodorizing, indicating, etc., applications. It is also possible for the cap to contain no holes where venting is not desired, e.g., where the component in the chamber is a device or material for indicating the state of the container interior, e.g., pressure, gas content ($CO$, $NO_x$, etc.), in which case the cap can also be transparent at least at a portion thereof.

In accordance with a preferred embodiment, the component is a filter element made of activated carbon, most preferably of a carbon-carbon or other composite. See U.S. Pat Nos. 4,500,328, 4,772,508, 4,391,873 and 4,152,482 and U.S. application Ser. No. 013,501, filed on Feb. 11, 1987, now allowed. Sintered metal, porous plastic, porous ceramic or other materials commonly used as filter elements are also employable.

The instant invention further contemplates the combination of a container, such as a bag or the like; a filter, such as the aforedescribed filter, and a filter-mounting assembly, such as the aforedescribed assembly.

Upon further study of the specification and appended claims, further objects and advantages of this invention will become apparent to those skilled in the art.

BRIEF DESCRIPTION OF THE DRAWINGS

Various other objects, features and attendant advantages of the present invention will be more fully appreciated as the same becomes better understood when considered in conjunction with the accompanying drawings, in which like reference characters designate the same or similar parts throughout the several views, and wherein.

DETAILED DESCRIPTION

Figure 1:
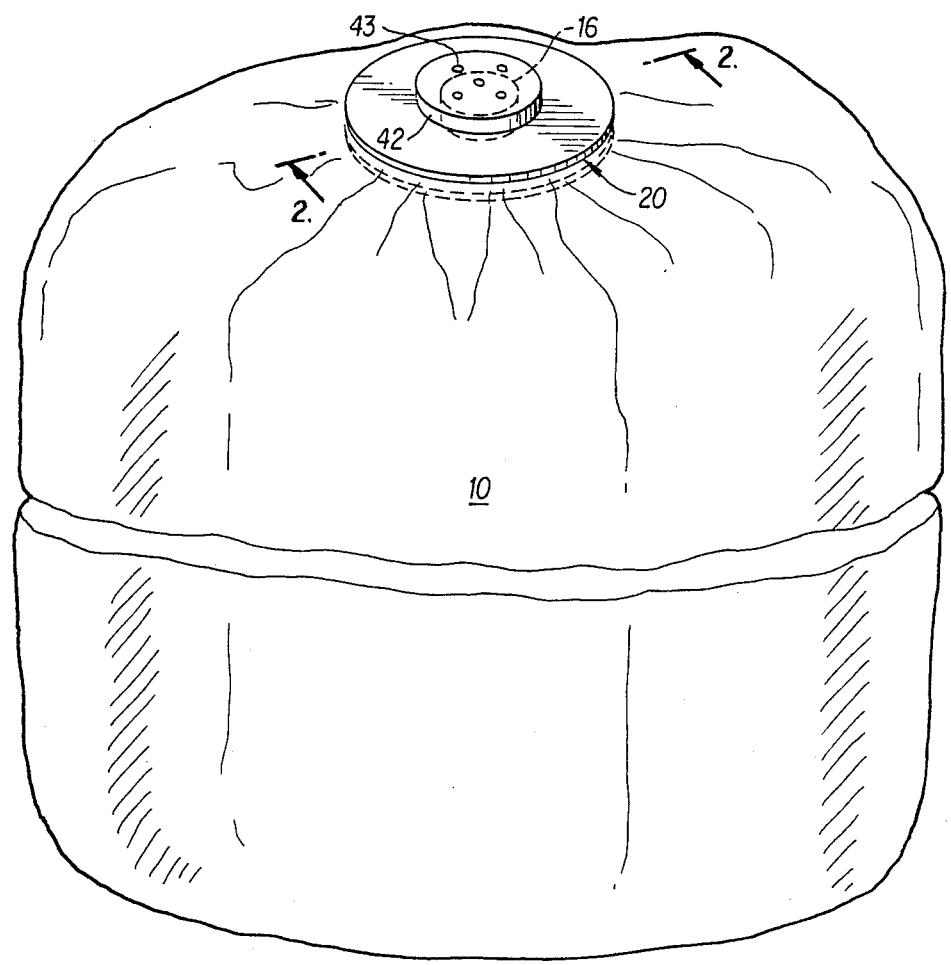
FIG. 1 is a perspective view showing a waste-containing bag vented through a component such as a filter retained by an assembly configured in accordance with the principles of the instant invention.

Referring now to FIG. 1, there is shown a plastic bag, designated generally by the numeral 10, which has stored therein waste material, which waste material may be, for example, nuclear waste material. The bag may be any size, e.g., of the 1 to 2-gallon variety or of a 15 or 20 gallon volume. The contained material may be in the form of particles, granules, powders, other solids, liquids and gases or mixtures thereof; or any other materials or objects, e.g., which have interstices which can contain gases, such as air or other gases, especially which also have suspended therein hazardous waste in the form of, for example, radioactive particles or gases. In order to avoid swelling and bursting of plastic bags as a result of storage over long periods of time, it is desirable to provide bags with at least one vent 12 so that pressure does not build up within them. This is an especially serious problem in the case of nuclear waste storage in that the gases from nuclear waste materials contain radioactive and thus hazardous particles. It is, of course, not desirable to release these gases into the atmosphere, e.g., since they can be inhaled and cause cancer such as lung cancer. The instant invention minimizes this danger by filtering the vent gases. In accordance with this preferred embodiment of the instant invention, the vent 12 includes a filter element 16, best shown in FIG. 2, which is retained in place by an assembly preferably made of plastic, but also of other material, e.g., metal, designated generally by the numeral 20, which fits within the vent 12 and seals with the bag 10 over areas of the bag adjacent the vent 12.

While the illustrated embodiment shows a single vent 12 and single filter assembly 20 for retaining a filter 16 in combination with a single bag 10, if necessary or desired the bag could have a plurality of vents each with a filter retained therein by a filter assembly configured in accordance with the principles of the instant invention. Moreover, not all assemblies of this invention on a given container such as a bag need have the same component or components. For example, some could contain filters and one an indicator of the state of the bag, one a deodorizer, etc.

Another use for the filter-retaining assembly 20 is with a colostomy bag. Using this invention, such a bag could contain a component such as those mentioned herein, e.g., a deodorizer and/or a filter. Thus, a colostomy bag could be vented through the top through a filter 16 secured in the bag vent 12 by a filter-mounting assembly 20. There are, of course, numerous applications for the filter- or other component-mounting assembly 20 in addition to radioactive waste disposal bags and colostomy bags, e.g., normal household garbage bags and other garbage containers, food containers, especially plastic walled containers, etc.

Figure 2:
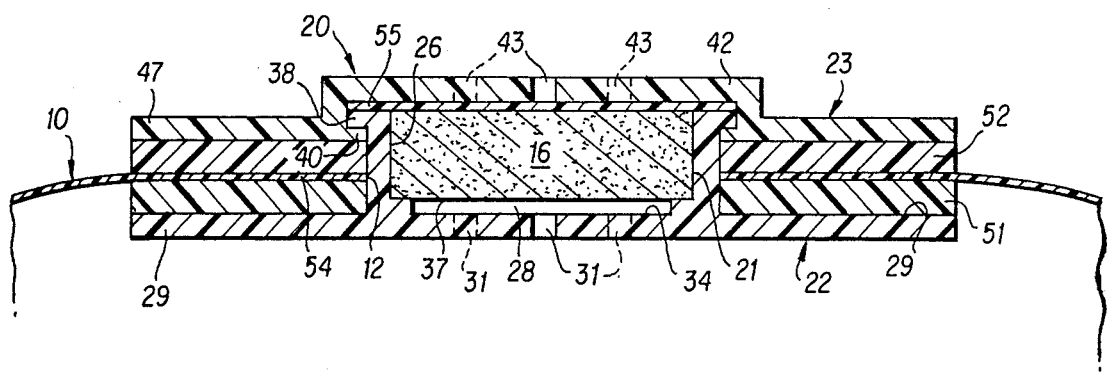
FIG. 2 is a cross-section taken along Line 2—2 of FIG. 1.
Figure 3:
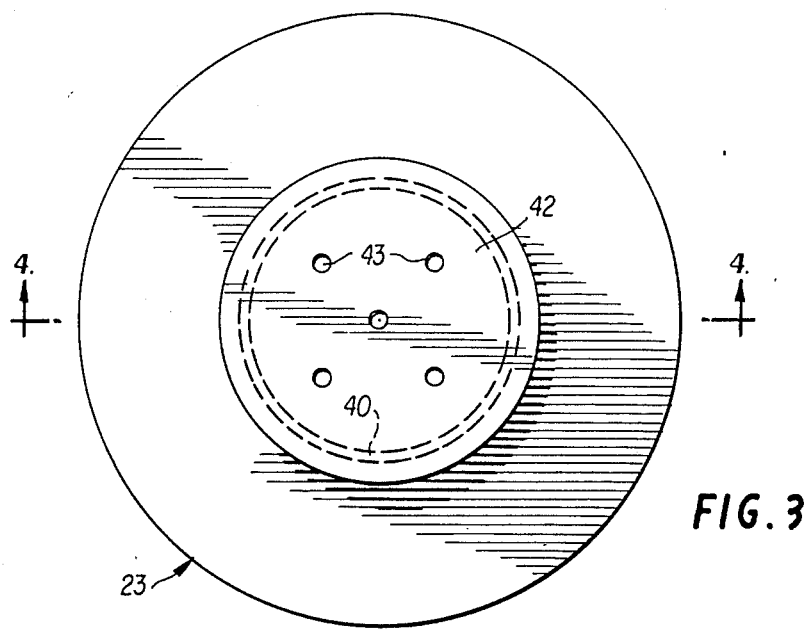
FIG. 3 is a top view of a retaining cap comprising a portion of the assembly.
Figure 4:
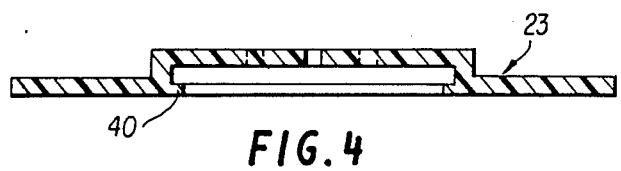
FIG. 4 is a cross-section taken along Line 4—4 of FIG. 3.

Referring now more specifically to FIGS. 2-6, it is seen that a filter element 16 is preferably in the form of a disc made of porous, activated carbon-carbon composite; however, as mentioned, the filter element can be made of sintered metal, porous plastic, or porous ceramic, activated carbon, charcoal, etc. As is best seen in FIG. 2, the filter element or other component 16 is retained within a chamber 21 formed between a base plate, designated generally by the numeral 22, and a cap plate, designated generally by the numeral 23, which plates are held in spaced relation to one another by a projecting annular flange 26 projecting normally with respect to the plates when the plates are assembled as passing through the opening in the wall of the bag or other container, forming the vent 12.

Figure 5:
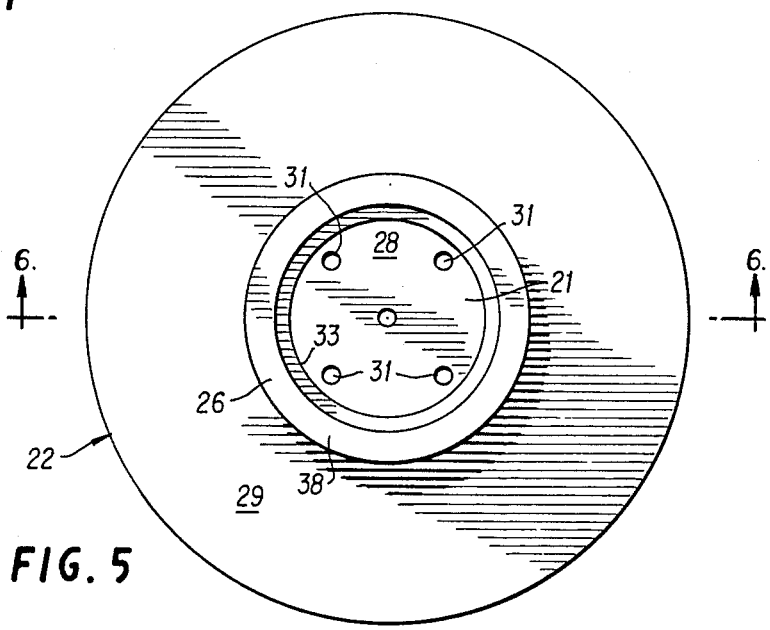
FIG. 5 is a top view of a base plate forming a portion of the assembly of the present invention.
Figure 6:
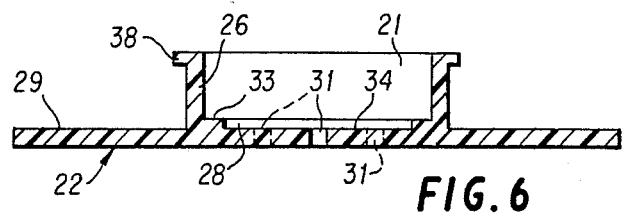
FIG. 6 is a cross-section taken along Line 6—6 of FIG. 5.

As is seen in FIGS. 5 and 6 when considered in conjunction with FIG. 2, the projecting annular flange 26 is preferably concentric with the base plate 22 and separates the base plate into a plenum portion 28 and a first flange portion or base rim flange 29. The plenum portion 28 forms the bottom of chamber 21, while, as will be explained hereinafter, the portions of the wall, e.g., of bag 10 adjacent the opening 12 overlie the base rim flange 29.

The plenum portion 28 preferably has a plurality of ports 31 therethrough so that gases within the bag 10 can pass into the chamber 21. An optional annular shelf 33 next to the projecting annular flange 26 provides a support surface which holds the filter or other element 16 in spaced relation with the floor 34 of the plenum portion 28 of the base plate 22 to allow gases passing through the ports 31 to distribute themselves adjacent the bottom surface 37 (see FIG. 2) of the element 16.

The projecting annular flange 26 has a lip 38 projecting radially therefrom and extending completely therearound. The lip 38 cooperates with a second lip 40 on the cap plate 23 (see FIG. 4) to retain the cap plate in place over the filter element 16. The cap plate 23 has a raised area 42 which forms the top of the filter element chamber 21. A plurality of ports 43 can be contained in cap plate 23, e.g., to allow gas which has been filtered by the filter element 16 to vent into the atmosphere. Any particles which may have radioactive debris thereon are trapped in the filter 16 so that gas escaping from the bag 10 is relatively free of radiation in a preferred embodiment. The cap plate 23 also has a second flange portion or cap rim flange 47, which complements base rim flange 29 of the base plate 22 by overlapping base rim flange when the assembly 10 is assembled.

Preferably, disposed between the cap rim flange 47 and the base rim flange 29 are first and second plastic or other gaskets 51 and 52, respectively. The portion 54 of the bag 10 adjacent the vent opening 12 is preferably clamped between the gaskets 51 and 52 to provide a gas and liquid-tight seal.

In a preferred embodiment, e.g., in order to prevent ground water or other liquid from entering the storage container, such as bag 10, the filter or other component mounting assembly 20 can be provided with a liquid barrier, e.g., located at 55 which is gas and vapor-permeable. In the illustrated embodiment, the liquid barrier is positioned on the inner surface 56 of the cap plate 23 and abuts the outer surface 47 of the filter element 16. In other applications, such as a colostomy bag, it may be desirable to prevent liquid from emanating out of the container. Thus, the gas and vapor-permeable liquid barrier 55 could be positioned between the bottom surface 37 of the filter element 16 and the floor 34 of the plenum 28. Exemplary of gas and vapor-permeable materials which are liquid barriers are Gortex ® (U.S. Pat. No. 3,953,566).

In one embodiment of the invention, the entire assembly has a diameter of approximately 2⅛ inches with the filter element having a diameter of approximately ⅞ inch. The thickness of each assembly is approximately ⅜ inch. The cap plate 23 and base plate 22 are made of corrosion-resistant resilient plastic material so that the plates snap together with the lip 38 snapping over lip 40 when the two elements are pressed together. The lips 38 and 40 can be made readily deformable, e.g., by providing a thickness and length of about 1/32 of an inch. Of course, none of these dimensions is critical, nor is the overall size, but for a given application will be chosen appropriately using routine considerations. Similarly, the shape of the assembly of this invention is not critical, e.g., it is not necessarily circular.

As mentioned, the component contained in the chamber of this invention is preferably a filter, but can be any component desired, e.g., an indicator, e.g., of the status of the interior of the bag, e.g., the radioactivity level, gas pressure, gas contents, temperature, etc., chemical reactants, e.g., for treating gas emanating through the assembly, desiccants, adsorbents, absorbents, deodorizers, etc.

From the foregoing description, one skilled in the art can easily ascertain the essential characteristics of this invention and, without departing from the spirit and scope thereof, can make various changes and modifications of the invention to adapt it to various usages and conditions.

All patents, publications and applications mentioned herein are entirely incorporated by reference herein.

What is claimed is:

1. An assembly for retaining a filter element in alignment with an opening through a wall, comprising:
    a base plate for positioning on one side of the wall in alignment with the opening, the base plate having a projecting flange for passage through the opening, the projecting flange defining a sidewall of a chamber for receiving said filter element and the projecting flange being positioned inboard of the periphery of the base plate to define a first flange portion between the periphery and the projecting flange, the base plate having a vented floor portion;
    a cap plate comprising a second flange portion and a vented center portion, the cap plate cooperating in fixed relation with the base plate to close the chamber containing the filter element to retain the filter element therein, with the second flange portion on the cap plate being in alignment with the first flange portion on the base plate; and
    sealing means disposed between the first and second flange portions for sealing engagement with opposite surfaces of the wall adjacent the opening.

2. The assembly of claim 1, wherein the vented floor of the base plate has holes therethrough effective to permit flow of the gas from one side of the base plate to the other.

3. The assembly of claim 2, wherein said vented center portion of the cap plate has holes effective to permit flow of gas from one side of the cap plate to the other.

4. The assembly of claim 1, wherein said filter element is composed of optionally activated carbon-carbon composite material.

5. The assembly of claim 1, further including a gas permeable liquid barrier retained by the assembly in juxtaposition with said vented floor of the base plate.

6. The assembly of claim 1, further including a gas permeable liquid barrier retained by the assembly in juxtaposition with said vented portion of the cap plate.

7. The assembly of claim 1, wherein the element chamber and the first and second flange portions are circular.

8. The assembly of claim 7, wherein said sealing means comprises a first annular gasket positioned in abutment with the first flange portion and a second annular gasket positioned in abutment with the second flange portion, the wall of the container being sandwiched between the first and second annular gaskets.

9. The assembly of claim 1, wherein the base plate and cap plate are made substantially of plastic.

10. The assembly of claim 1, wherein said wall is a wall of a plastic bag and said assembly is made substantially of plastic.

11. The assembly of claim 1, wherein the projecting flange of the base plate includes a first peripheral lip which cooperates with a complementary second lip on the cap plate to hold the cap plate on the base plate so as to close the chamber containing the filter element.

12. In combination:
    a container having a wall defining a container interior, said wall having an opening and an assembly for retaining a filter element in alignment with said opening, the assembly comprising:
    a base plate for positioning on one side of the wall in alignment with the opening, the base plate having a projecting flange for passage through the opening, the projecting flange defining a sidewall of a chamber for receiving said filter element and the projecting flange being positioned inboard of the periphery of the base plate to define a first flange portion between the periphery and the projecting flange, the base plate having a vented floor portion;
    a cap plate comprising a second flange portion and a vented center portion, the cap plate cooperating in fixed relation with the base plate to close the chamber containing the filter element to retain the filter element therein, with the second flange portion on the cap plate being in alignment with the first flange portion on the base plate; and
    sealing means disposed between the first and second flange portions for sealing engagement with opposite surfaces of the wall adjacent the opening.

13. The combination of claim 12, wherein the vented floor portion of the base plate has holes therethrough effective to permit flow of gas from one side of the base plate to the other.

14. The combination of claim 13, wherein the vented center portion of the cap plate has holes effective to permit flow of gas from one side of the cap plate to the other.

15. The combination of claim 14, wherein said filter element is composed of optionally activated carbon-carbon composite material.

16. The combination of claim 12, further including a ga permeable liquid barrier retained by the assembly in juxtaposition with said vented floor of the base plate.

17. The combination of claim 12, wherein said sealing means comprises a first annular gasket positioned in abutment with teh first flange portion and a second annular gasket positioned in abutment with the second flange portion, the wall of the container being sandwichable between the first and second annular gaskets.

18. The combination of claim 12, wherein said container is a plastic bag and said assembly is made substantially of plastic.

19. The combination of claim 18, wherein said bag is a nuclear waste bag or a colostomy bag.

20. The combination of claim 12, wherein the projecting flange of the base plate includes a first peripheral lip which cooperates with a complementary second lip on the cap plate to hold the cap plate on the base plate so as to close the chamber containing the filter element.

21. The combination of claim 19, wherein said filter element is made of carbon-carbon composite material.

22. A combination of claim 21, further including a gas permeable liquid barrier retained by the assembly in juxtaposition with said vented center portion of the cap plate.

23. An assembly of claim 21, wherein said filter element has covering one surface thereof a gas permeable liquid barrier.

24. A container for containing nuclear waste material comprising:

a plastic bag for completely enclosing nuclear waste material, the plastic bag having an opening therein;

an assembly for retaining a filter element in alignment with said opening, wherein the assembly comprises:

a base plate for positioning on one side of the wall in alignment with the opening, the base plate having a projecting flange for passage through the opening, the projecting flange defining a sidewall of a chamber for receiving said filter element and the projecting flange being positioned in-board of the periphery of the base plate to define a first flange portion between the periphery and the projecting flange, the base plate having a vented floor portion;

a cap plate comprising a second flange portion and a vented center portion, the cap plate cooperating with the base plate to close the chamber containing the filter element to retain the filter element therein, with the second flange portion on the cap plate being in alignment with the first flange portion on the base plate;

sealing means disposed between the first and second flange portions for sealing engagement with the opposite surface of the wall adjacent the opening to keep nuclear waste material and gases therein from bypassing the filter element; and a gas-permeable liquid barrier covering at least one surface of the filter element.

* * * * *